United States Patent
Fändriks et al.

[11] Patent Number: 5,900,428
[45] Date of Patent: May 4, 1999

[54] PHARMACOLOGICAL USE OF AII-RECEPTOR ANTAGONISTS

[75] Inventors: Lars Fändriks, Askim; Anders Pettersson, Kode; Anders Åneman, Göteborg, all of Sweden

[73] Assignee: Astra Aktiebolag, Sodertalje, Sweden

[21] Appl. No.: 08/696,971

[22] PCT Filed: May 8, 1996

[86] PCT No.: PCT/SE96/00602

§ 371 Date: Aug. 28, 1996

§ 102(e) Date: Aug. 28, 1996

[87] PCT Pub. No.: WO96/36336

PCT Pub. Date: Nov. 21, 1996

[30] Foreign Application Priority Data

May 19, 1995 [SE] Sweden .................................. 9501881

[51] Int. Cl.⁶ .................................................. A61K 31/41

[52] U.S. Cl. ........................ 514/381; 514/269; 514/303; 514/258; 514/311; 514/210; 514/921

[58] Field of Search ..................... 514/397, 210, 514/921, 381, 269, 303, 258, 311

[56] References Cited

U.S. PATENT DOCUMENTS 5,155,118  10/1992  Carini et al. .
5,538,991   7/1996  Ashton et al. ............................ 514/397

FOREIGN PATENT DOCUMENTS 0459136  12/1991  European Pat. Off. .

*Primary Examiner*—Keith D. MacMillan
*Attorney, Agent, or Firm*—White & Case L.L.P.

[57] ABSTRACT

A method for the prophylaxis and treatment of MOF using certain angiotensin II type 1 receptor antagonists and a pharmaceutical preparation comprising these compounds.

2 Claims, No Drawings

PHARMACOLOGICAL USE OF AII-RECEPTOR ANTAGONISTS

This application is A 371 of PCT/SE96/00602, filed May 8, 1996, which claims priority to Sweden 95 01881-8, filed May 19, 1995.

FIELD OF THE INVENTION

The present invention is related to the use of angiotensin II type 1 receptor antagonists for the prophylaxis and/or treatment of multiple system organ failure (MOF) and to the manufacture of pharmaceutical preparations with effects on MOF.

BACKGROUND OF THE INVENTION

Angiotensin II type 1 receptor antagonists for which the present invention has found a new pharmacological use are known in the art. However, nothing has been reported or is known concerning the pharmacological and/or therapeutic properties of these compounds with respects to effect on MOF.

In connection with the present invention an angiotensin II type 1 of the general formula I is employed:

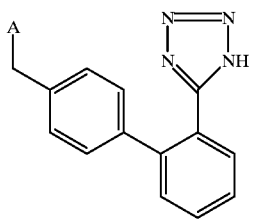

wherein A is

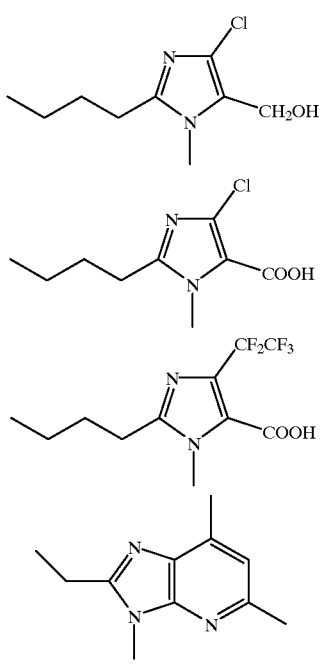

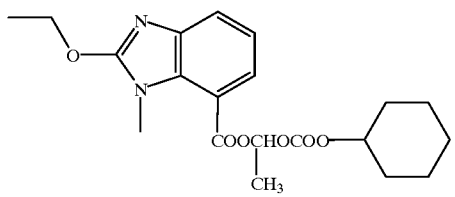

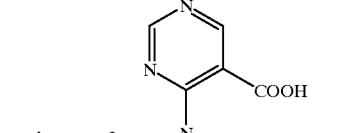

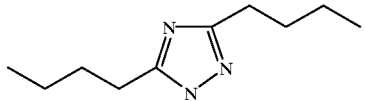

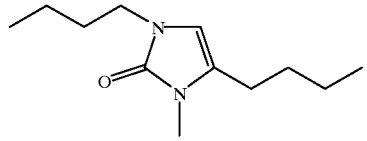

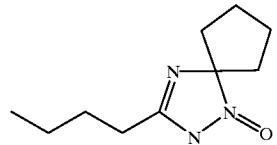

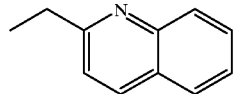

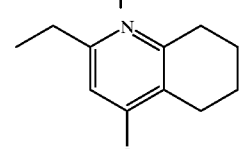

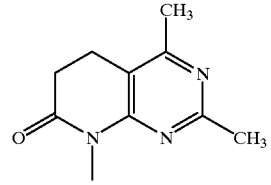

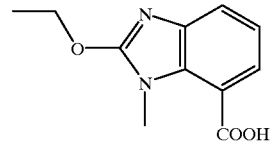

The compounds listed above may be used in racemic form or in the form of a substantially pure enantiomer; they may be used in neutral form or in the form of a salt, preferably a physiologically acceptable salt such as sodium, potassium, ammonium, calcium or magnesium. Where applicable the compounds listed above can be used in hydrolysable ester form.

The compound of the formula I wherein A is the I:1 moiety has the generic name losartan and is known from European patent no 253 310.

The compound of the formula I wherein A is the I:5 moiety has the generic name candesartan cilexetil, code no TCV-116 and is known from European patent no 459 136.

The compound of the formula I wherein A is the I:9 moiety is known under the generic name irbesartan.

The compound of the formula I wherein A is the I:13 moiety has the generic name candesartan and is known from European patent no 459 136.

Hemorrhage and/or trauma elicits a vasoconstrictive response that preferentially reduces blood flow to mesenteric organs. If severe, hemorrhage may propagate to circulatory shock, a condition in which oxygen delivery becomes insufficient to maintain tissue integrity and function. Manifestations of circulatory shock in mesenteric organs include collapse of the gut permeability barrier, enabeling gut pathogens to cross the intestinal mucosa and eventually spread to systemic compartments via lymphatics and blood vessels. The barrier dysfunction with microbial translocation, together the initially compromised systemic circulation, leads to functional failure of various organ systems (e.g. kidneys, heart, lungs, hemostasis). Such a sequential development of devastating sequele is defined as multiple system organ failure (MOF).

The treatment of MOF is very costly and results in long term treatments at intensive care units. Therapeutic efforts in MOF treatment today are aimed at life sustaining treatments, such as antibiotics, blood volume expansion and respiration assistance. However, a therapeutical approach in order to maintain mesenteric blood flow and oxygen delivery is not available today.

Reduction of mesenteric blood flow in the critically ill patient is mainly mediated by activation of the renin-angiotensin system with elevated plasma angiotensin II (AII) levels. Administration of compounds which blocks the formation of AII (i.e. angiotensin converting enzyme inhibitors, (ACE-inhibitors) have been shown to improve mesenteric oxygenation during severe shock.

The use of ACE inhibitors for treatment of severe shock is, however hampered by the fact that they act as nonspecific enzyme inhibitors and result in the accumulation of several vasoactive peptides e.g. (bradykinin, subst. P, endogenous opoids). This consequence may lead to an instable blood pressure regulation as well as increased risk for allergic manifestations and upper airway irritation.

It will be appreciated therefore that there is need for alternative and improved methods for the prophylaxis and/or treatment of multiple system organ failure.

DISCLOSURE OF THE INVENTION

It has unexpectedly been found that known compounds of the general formula

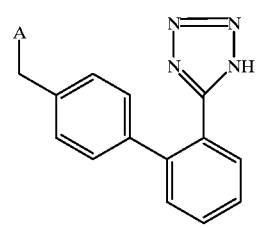

I wherein A is

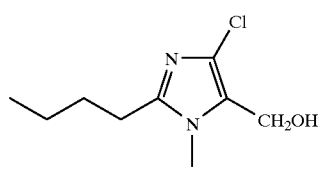

I:1

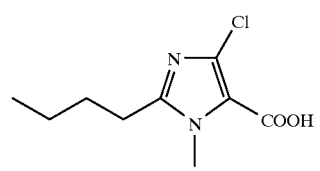

I:2

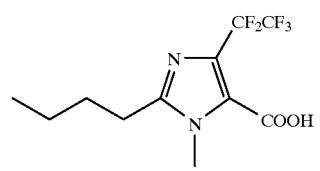

I:3

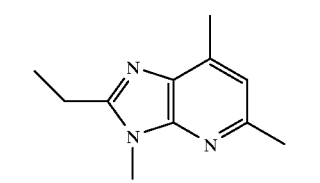

I:4

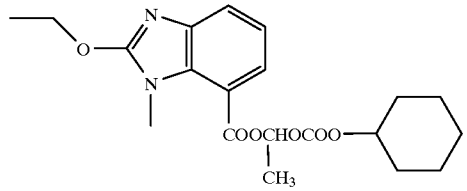

I:5

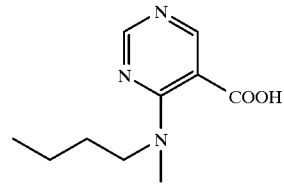

I:6

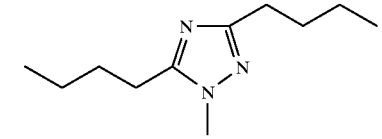

I:7

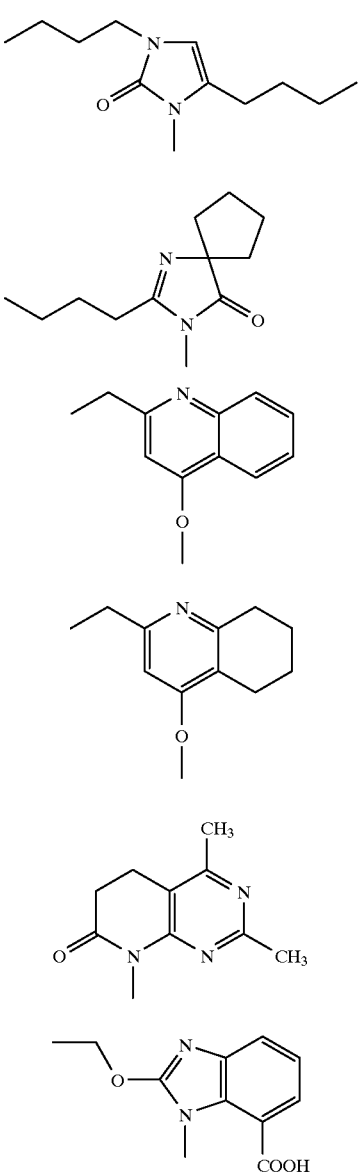

or a physiologically acceptable salt and/or a stereochemical isomer thereof are effective in the prophylaxis and/or treatment of multiple system organ failure (MOF).

It has been found that pharmacological specific blockade of AII type 1 receptors with a compound according to formula I has a surprisingly good effect on gastro-intestinal tissue oxygenation during conditions comparable to the situation in the critically ill patient. In addition, during conditions with elevated plasma AII concentrations, such a specific blockade of AII type 1 receptors was shown to reinforce the mucosal barrier function ill the upper gastrointestinal tract.

The present invention is based on our surprising finding that administration of specific AII type 1 receptor antagonists, which have the effect of maintained oxygen delivery and positive stimiulation of the gastrointestinal mucosal barrier, are useful for the prophylaxis and/or treatment of multiple system organ failure.

The compounds of the formula I can be administered orally, rectally or parenterally in neutral form or in the form of a salt. While the effects on splanchnic oxygenation and barrier function have been established in animals by the intravenous route, it is believed that the effect is a systemic effect which is not dependent on the mode of administration which is used, and accordingly the effects will be seen also with other routes of administration such as rectal or oral administration.

The dose of a compound according to formula I to be administered for prophylaxis and/or treatment of multiple system organ failure will vary depending on factors, such as the severity of the disease and the status of the patient. The dosage range at oral, rectal as well as intravenous administration will be in the range from 1 to 500 mg per day.

The preferred mode of the invention is the use of a compound of the formula I wherein A is I:1 (Losartan) or I:5 (TCV-116).

Scientific tests

Animal experiments have been performed during conditions comparable to the situation in the critically ill patient as described in Åneman et al 1995; Anesth. Analg. No 80, p 135–142. Gastrointestinal oxygenation was studied in anestethized pigs during an acute bleeding (40% of estimated blood volume). In an untreated group of animals (n=6) a profund decrease in mesenteric oxygenation was observed following 40% hemorrhage. In the losartan treated animal (n=5) no decrease in mesenteric oxygen delivery was seen following a 40% hemorrhage.

The ability to neutralize acid is an important component of the gastrointestinal mucosal barrier functions, particularly in the upper gut but also in lower parts. The following experiments were performed in the anesthetized rat duodenum- Intravenous administrations of AII were followed by a decreased ability to neutralize luminal acid in the untreated animals (n=6). This inhibition was, surprisingly, reversed to an enhanced acid neutralisating capacity in response to the same dose AII after pretreatment with the AII-receptor blocker losartan (n=6).

Pharmaceutical preparations

Conventional pharmaceutical preparations can be used. The pharmaceutical preparations are preferentially in the form of injection solutions, but it is also possible to use other kinds of preparation, such as oral solutions, or suspensions, tablets or capsules. Alternative routes of administrations are sublingual tablets or solutions and rectal solutions, suspensionsor or rectiols.

The pharmaceutical preparation contains between 1 mg and 500 mg of active substance, preferably 10 to 250 mg.

We claim:

1. A method for the prophylaxis and/or treatment of multiple system organ failure in mammals, which comprises administering to a mammalian host in need of such prophylaxis and/or treatment a compound of formula I

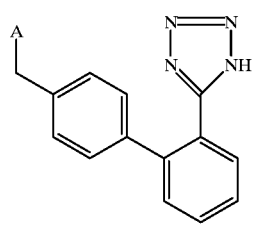

or a physiologically acceptable salt and/or stereochemical isomer thereof wherein A is selected from the group consisting of

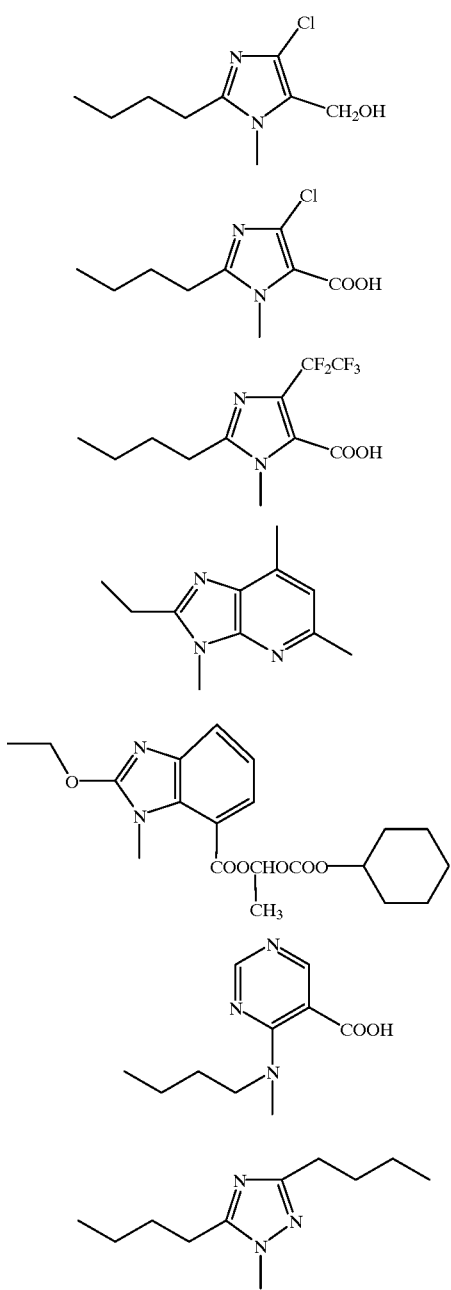
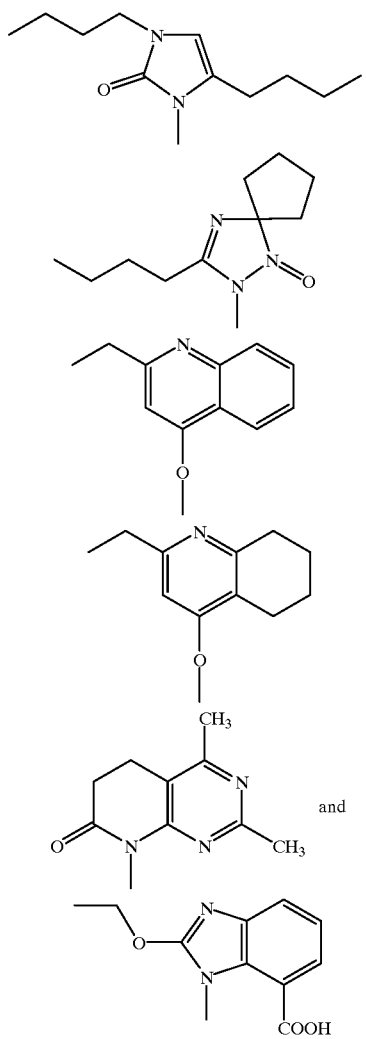
2. A method according to claim 1, which comprises administering a compound of formula I wherein A is the I:1 or I:5 moiety.
* * * * *

UNITED STATES PATENT AND TRADEMARK OFFICE
CERTIFICATE OF CORRECTION

PATENT NO. : 5,900,428
DATED : May 4, 1999
INVENTOR(S) : Blackburn et al.

It is certified that error appears in the above-identified patent and that said Letters Patent is hereby corrected as shown below:

Col. 8, lines 8-15 (Claim 1), change the formula

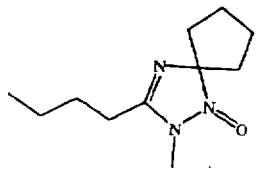 " to -- 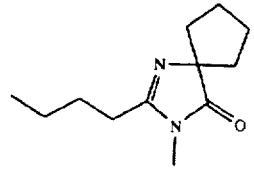 --.

Signed and Sealed this

Twenty-third Day of November, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,900,428
DATED : May 4, 1999
INVENTOR(S) : Fändriks et al.

It is certified that error appears in the above-indentified patent and that said Letters Patent is hereby corrected as shown below:

Col. 8, lines 8-15 (Claim 1), change the formula

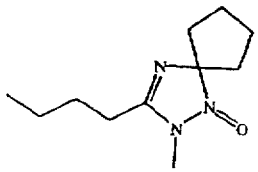 to 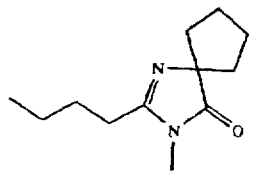.

This certificate supersedes Certificate of Correction issued November 23, 1999.

Signed and Sealed this

Eleventh Day of April, 2000

Attest:

Attesting Officer

Q. TODD DICKINSON
Director of Patents and Trademarks